(12) United States Patent
Kaneda et al.

(10) Patent No.: US 6,596,285 B2
(45) Date of Patent: *Jul. 22, 2003

(54) EMULSIFIED COSMETIC FACE PACK

(75) Inventors: Isamu Kaneda, Yokohama (JP);
Fumiaki Matsuzaki, Yokohama (JP);
Toshio Yanaki, Yokohama (JP);
Toshihito Yabu, Yokohama (JP)

(73) Assignee: Shiseido Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 58 days.

(21) Appl. No.: 09/308,678

(22) PCT Filed: Oct. 29, 1998

(86) PCT No.: PCT/JP98/04906

§ 371 (c)(1),
(2), (4) Date: Jun. 7, 1999

(87) PCT Pub. No.: WO99/22695

PCT Pub. Date: May 14, 1999

(65) Prior Publication Data

US 2001/0006661 A1 Jul. 5, 2001

(30) Foreign Application Priority Data

Oct. 31, 1997 (JP) ............................................. 9-316411

(51) Int. Cl.[7] ............................ A61K 7/00; A61K 7/035

(52) U.S. Cl. .......................................... 424/401; 424/69

(58) Field of Search .................... 424/401, 69; 514/784, 514/785, 844, 845, 846, 847, 848, 873

(56) References Cited

U.S. PATENT DOCUMENTS 5,080,889 A * 1/1992 Katada et al. ................. 424/63
5,641,495 A * 6/1997 Jokura et al. ................ 424/401
5,688,493 A * 11/1997 Sugawara et al. ............. 424/61

FOREIGN PATENT DOCUMENTS

| EP | 0697212 A | 2/1996 |
|----|-----------|--------|
| JP | 05194180 | 8/1993 |
| WO | WO 9316684 A | 9/1993 |

OTHER PUBLICATIONS

STN International Karlsruhe; File CA, XP002121317 & JP 63 057508A, Mar. 12, 1998; Japanese Abstract.
STN International Karlsruhe; File CA, XP002121318 & JP 07 082129, Mar. 28, 1995; Japanese Abstract.

* cited by examiner

Primary Examiner—Thurman K. Page
Assistant Examiner—S. Tran
(74) Attorney, Agent, or Firm—Townsend & Banta

(57) ABSTRACT

The present invention is an emulsion-type pack cosmetic containing polyvinyl alcohol, oil, and water which characteristically contains the oil in the amount of 20–80 wt % or 15–50 wt % of the total emulsion-type pack cosmetic. A fast-drying peel-off type pack cosmetic with a short drying time and superior usability can be provided.

12 Claims, No Drawings

EMULSIFIED COSMETIC FACE PACK

FIELD OF THE INVENTION

The present invention relates in general to a pack cosmetic, and more particularly to a peel-off emulsion-type pack cosmetic which exhibits a shorter drying time after application of the pack and superior usability.

BACKGROUND OF THE INVENTION

A pack cosmetic is widely used for the purpose of moisture retention and cleaning of the skin. There are several types according to how they are used including the peel-off type, wipe-off or rinse-off type, and pasting type.

Of these, the peel-off type, which is applied on the skin, dried to form a film, and then peeled off, is used a great deal because it exhibits the superior effect of removing smudges on the skin surface, old corneum, black stains on the pores, and keratotic plugs, and gives a high level of satisfaction at the time of use.

However, the peel-off type pack cosmetic has a shortcoming in that the let-stand time (or drying time) after application is long. A single use usually takes about 30 minutes, which is a hindrance to the use of a pack cosmetic in busy daily life. Because of this, several attempts to make the drying time shorter than the conventional duration have been made. For example, the drying time can be shortened by increasing the alcohol content in the formulation. However, in this case, there is a problem in that a higher alcohol concentration stimulates the skin and/or eyes and such. The drying time can also be shortened by, for example, blending in a large amount of powder and such to reduce the amount of water in the formulation, or adding a substance which interacts with the film agent to form a gel to promote the film formation during the drying time. However, each of these cases have a problem in terms of stability because, for example, the product in storage hardens over time due to gelation. As described thus far, it has been difficult to obtain a peel-off type pack cosmetic which has a short drying time and is free of problems as a product.

In light of the aforementioned situation, the inventors conducted earnest research to obtain a fast drying pack cosmetic which has a short drying time and is free of problems as a product, and, amazingly, discovered that a peel-off type pack cosmetic with a short drying time and superior usability with very smooth peeling can be obtained as an emulsion-type pack cosmetic containing polyvinyl alcohol, oil, and water if the oil content is adjusted to 20–80 wt % or 15–50 wt % of the total emulsion-type pack cosmetic and, preferably, a surfactant is contained as well, thus completing the present invention.

The object of the present invention is provide a fast-drying peel-off type pack cosmetic which has a short drying time and superior usability.

DISCLOSURE OF THE INVENTION

That is, the present invention provides an emulsion-type pack cosmetic containing polyvinyl alcohol, oil, and water which characteristically contains the oil in the amount of 20–80 wt % of the total emulsion-type pack cosmetic.

Also, the present invention provides an emulsion-type pack cosmetic containing polyvinyl alcohol, oil, and water which characteristically contains the oil in the amount of 15–50 wt % of the total emulsion-type pack cosmetic.

Furthermore, the present invention provides an emulsion-type pack cosmetic containing polyvinyl alcohol, oil, and water which characteristically contains the oil in the amount of 25–40 wt % of the total emulsion-type pack cosmetic.

Also, the present invention provides said emulsion-type pack cosmetic which additionally contains a surfactant.

Furthermore, the present invention provides said emulsion-type pack cosmetic wherein the content of said surfactant is 1–20 wt % of the total emulsion-type pack cosmetic.

THE BEST MODES OF THE EMBODIMENTS

The configuration of the present invention is described in detail below.

The polyvinyl alcohol used in the present invention functions as a film agent and emulsifying agent of the emulsion-type pack cosmetic, and its selection is not limited as long as it acts as a film agent and emulsifying agent. A commercially available polyvinyl alcohol, for example, can be used.

Commercially available polyvinyl alcohols are divided into several grades based on differences in the degree of polymerization and the degree of saponification. The degree of polymerization is usually indicated by the viscosity measurement of a 4%-concentration aqueous solution at 20° C. For the present invention, those with a low viscosity of 4 cps to a high viscosity of 70 cps can be used. However, the formed film tends to become stronger and the viscosity of the pack increases as the degree of polymerization becomes higher. Therefore, considering the adequate strength of the film and the viscosity which makes pack application easy, it is preferable to use polyvinyl alcohol in the viscosity range of 30–50 cps.

On the other hand, the degree of saponification is defined based on different saponification ratios of the acetyl groups in polyvinyl acetate when manufacturing polyvinyl alcohols, which is largely divided into the complete saponification type which is saponified almost completely (98–100%), and "the partial saponification type", which is partially saponified (87–89%) with some remaining acetyl groups. Although both saponification types can be used in the present invention, the partial saponification type has a higher solubility at room temperature, better viscosity stability at lower temperatures, and a superior ability to emulsify the blended oil, and therefore it is preferable to use the partial saponification type polyvinyl alcohol.

The blend ratio of the aforementioned polyvinyl alcohol is preferably 5–20 wt %, more preferably 9–15 wt %, of the total amount of the pack cosmetic. If the blend ratio is less than 5 wt %, then a film with adequate strength will not form and even peeling will be difficult. On the other hand, if the blend ratio is more than 20 wt %, then the viscosity will be too high and application may not be easy.

The oil used in the present invention is not limited in particular, and any oil which is used in emulsified cosmetics can be used. Examples include natural animal/plant oils/fats such as macadamia nut oil, evening primrose oil, olive oil, mink oil, jojoba oil, lanolin, and squalene; hydrocarbons such as liquid petrolatum, squalane, and petrolatum; higher alcohols such as cetanol, stearyl alcohol, and cetyl alcohol; higher fatty acids such as myristic acid, palmitic acid, stearic acid, behenic acid, isostearic acid, oleic acid, linolic acid, linolenic acid, and oxystearic acid; esters such as pentaerythritol tetra 2-ethylhexanoate, isopropylmyristic acid, isopropylpalmitic acid, isopropylstearic acid, and glyceryl 2-ethylhexanoate; diorgano polysiloxanes with low to high viscosity such as dimethyl polysiloxane, methylphenyl polysiloxane, methylhydrogen polysiloxane and dimethyl siloxane/methylphenyl polysiloxane copolymer, cyclic siloxanes such as octamethylcyclotetrasiloxane, decamethylcyclopentasiloxane and tetramethyltetraphenyltetracyclosiloxane, cyclic siloxane solutions such as high polymer gum-like dimethyl polysiloxane, gum-like dimethylsiloxane/methylphenylsiloxane copolymer and gum-like dimethyl polysiloxane, diorgano polysiloxane containing alkyl groups with a carbon number of 6–50, and silicone oils such as amino modified silicone, alkylated silicone and fluorine modified silicone. One or more of these oils can be blended in. Using volatile silicone oil is preferable in terms of the sensation at the time of application. It is also possible to give a moist feeling to the skin after peeling by adding natural animal/plant oils/fats.

The blend ratio of the oil is 20–80 wt % or 15–50 wt % of the total amount of the emulsion-type pack cosmetic. If it is less than 15 wt % then the fast drying effect will be poor, and blending more than 50 wt % or 80 wt % results in a high viscosity, sometimes causing a problem in terms of usability at the time of application. From the usability point of view in particular, 25–40 wt % is preferable. Water which is used in the present invention is stirred and mixed with the aforementioned essential ingredients to form an emulsified composition, from which the emulsion-type pack cosmetic of the present invention can be manufactured with a conventional method. The blend ratio of water is not limited in particular, but usually 30–60 wt % of the total amount of the emulsion-type pack cosmetic is preferable. As the blend ratio of the oil increases, the water content decreases in comparison. However, there is no difference in the water evaporation rates of the pack cosmetics with various blend ratios, which indicates that the fast drying properties due to blending of the oil is not related to the water content.

In the present invention, it is preferable to additionally blend in a surfactant. The addition of a surfactant to the emulsion-type pack cosmetic of the aforementioned composition has a significant effect in terms of the drying time and usability.

The selection of the surfactant for use in the present invention is not limited in particular. Nonionic surfactants (hydrophilic or lipophilic) are preferable. Specific examples include POE-sorbitan fatty acid esters including POE-sorbitan monooleate, POE-sorbitan monostearate, POE-sorbitan monooleate and POE-sorbitan tetraoleate, POE-sorbitol fatty acid esters including POE-sorbitol monolaurate, POE-sorbitol monooleate, POE-sorbitol pentaoleate and POE-sorbitol monostearate, POE-glycerol fatty acid esters including POE-glyceryl monostearate, POE-glyceryl monoisostearate and POE-glyceryl triisostearate, POE-fatty acid esters including POE-monooleate, POE-distearate, POE-monodioleate and ethylene glycol distearate; POE-alkyl ethers including POE-lauryl ether, POE-oleyl ether, POE-stearyl ether, POE-behenyl ether, POE2-octyldodecyl ether and POE-cholestanol ether, pluaronics including pluronic, POE-POP alkyl ethers including POE-POP cetyl ether, POE-POP2-decyltetradecyl ether, POE-POP monobutyl ether, POE-POP lanolin hydrate and POE-POP glycerol ether, tetra POE-tetra POP ethylenediamine condensates including tetronic, POE-castor oil hydrogenated castor oil derivatives including POE-castor oil, POE-hydrogenated castor oil, POE-hydrogenated castor oil monoisostearate, POE-hydrogenated castor oil triisostearate, POE-hydrogenated castor oil monopyroglutamate monoisostearate, POE-hydrogenated castor oil maleate, POE beeswax/lanolin derivatives including POE sorbitol beeswax, alkanol amides including coconut fatty acid diethanol amide, lauric acid monoethanol amide and fatty acid isopropanol amide; as well as POE-propylene glycol fatty acid ester, POE-alkyl amine, POE-fatty acid amide, sucrose fatty acid ester, POE nonylphenylformaldehyde condensate, alkylethoxydimethylamine oxide and trioleyl phosphate.

The blend ratio of the surfactant is not limited in particular. A preferable blend ratio range is 1–20 wt %, more preferably 3–10 wt %, of the total amount of the emulsion-type pack cosmetic. If the blend ratio is less than 1 wt % then the improvement in the usability and drying time may not be easily attained. If it is more than 20 wt %, then the viscosity becomes too high and the usability may be affected.

Although an emulsion-type pack cosmetic containing polyvinyl alcohol, oil, and water is prior art, the conventional emulsion-type pack cosmetic has an oil content of approximately 10 wt % or less, and there is no case where 15 wt % or more oil is blended in. An emulsion-type pack cosmetic which has an oil content of 15 wt % or more and also contains a surfactant is new also as an emulsified composition for cosmetics, and the present invention is the first case which uses said emulsified composition for a cosmetic.

In addition to the aforementioned essential ingredients, ingredients which are normally blended into cosmetics can be blended in the pack cosmetic of the present invention as necessary within the range that does not affect the effect of the present invention. Examples of ingredients which can be blended in include lower alcohols such as ethanol and isopropyl alcohol, polyhydric alcohols such as glycerine, propylene glycol, dipropylene glycol, 1,3-butanediol, sorbitol, and maltitol, powders such as talc, kaolin, titanium oxide, and silicic acid anhydride, water soluble polymers such as polyvinyl pyrolidone, polyvinyl acetate, carboxymethyl cellulose, and xanthan gum, preservatives, disinfectants, ultraviolet light absorbents, chelating agents, antioxidants, and perfumes.

EXAMPLES

The present invention is described in detail by referring to examples below. The present invention is not limited to these examples. The blend ratios in the examples are indicated in weight percent units. The emulsion-type pack cosmetics prepared in the examples were evaluated for their drying time and usability using the following evaluation methods.

[Measurement of the Drying Time]

The drying time of the pack cosmetics was measured based on sensory evaluation by a panel of ten female specialists who used the pack cosmetics of Examples and Comparative examples. The measurements were conducted in a thermo-hygrostatic room with a temperature of 25° C. and a relative humidity of 40%. Each panelist applied a sample evenly on her face and recorded the drying time in minute units by determining the time of complete drying as when the applied pack was not sticky when touched by a finger and could be peeled off as one sheet of film. Data from 10 panelists were averaged to obtain the drying time.

[Usability Test]

A panel of ten female specialists used the pack cosmetics of Examples and Comparative examples and conducted sensory testing of the usability of peeling off the dried pack based on the following criteria.

⊚: Eight or more out of ten reported that the pack was easy to peel off and usability was good.

◯: Six or more out of ten reported that the pack was easy to peel off and usability was good.

Δ: Four or more out of ten reported that the pack was easy to peel off and usability was good.

X: Less than four out of ten reported that the pack was easy to peel off and usability was good.

"The Invention Described in claim 1 in the Scope of the claim"

Pack cosmetics with the compositions listed in Table 1 and Table 2 were prepared and the aforementioned drying time test and usability test were conducted. The polyvinyl alcohol used had a degree of polymerization of 40 cps (20° C., 4% aqueous solution) and a degree of saponification of 88%.

TABLE 1

| Ingredient | Comparative example 1 | Example 1 | Example 2 | Example 3 | Example 4 | Example 5 | Example 6 | Example 7 |
|---|---|---|---|---|---|---|---|---|
| Polyvinyl alcohol | 14 | 12 | 10 | 9 | 8 | 6 | 5 | 3 |
| Propylene glycol | 5 | 5 | 5 | 5 | 5 | 5 | 5 | 5 |
| Ethanol | 5 | 5 | 5 | 5 | 5 | 5 | 5 | 5 |
| Squalane | 10 | 20 | 30 | 40 | 50 | 60 | 70 | 80 |
| Preservative | *1 | *1 | *1 | *1 | *1 | *1 | *1 | *1 |
| Purified water | *2 | *2 | *2 | *2 | *2 | *2 | *2 | *2 |
| Drying time (minutes) | 17 | 14 | 7 | 6 | 6 | 5 | 5 | 5 |
| Usability | Δ | ○ | ⊙ | ⊙ | ○ | ○ | ○ | Δ |

*1: Appropriate amount
*2: Balance

TABLE 2

| Ingredient | Comparative example 2 | Example 8 | Example 9 | Example 10 | Example 11 | Example 12 | Example 13 | Example 14 |
|---|---|---|---|---|---|---|---|---|
| Polyvinyl alcohol | 14 | 12 | 10 | 9 | 8 | 6 | 5 | 3 |
| Propylene glycol | 5 | 5 | 5 | 5 | 5 | 5 | 5 | 5 |
| Ethanol | 5 | 5 | 5 | 5 | 5 | 5 | 5 | 5 |
| Octamethyltetrasiloxane | 10 | 20 | 30 | 40 | 50 | 60 | 70 | 80 |
| Preservative | *1 | *1 | *1 | *1 | *1 | *1 | *1 | *1 |
| Purified water | *2 | *2 | *2 | *2 | *2 | *2 | *2 | *2 |
| Drying time (minutes) | 17 | 13 | 7 | 6 | 6 | 5 | 5 | 5 |
| Usability | Δ | ○ | ⊙ | ⊙ | ○ | ○ | ○ | Δ |

*1: Appropriate amount
*2: Balance

As clearly shown in Table 1 and Table 2, the emulsion-type pack cosmetics of Examples which contain 20–80 wt % of the oil have a very short drying time and superior usability when peeled off compared with those of Comparative examples prepared with conventional technology. The usability is particularly good when the oil content is 30–40 wt %.

"The Invention Described in claims 2–claim 5 in the Scope of the claim"

Pack cosmetics with the compositions listed in Table 3–Table 5 were prepared and the aforementioned drying time test and usability test were conducted. The polyvinyl alcohol used had a degree of polymerization of 40 cps (20° C., 4% aqueous solution) and a degree of saponification of 88%.

TABLE 3

| Formulation | Comparative example 3 | Example 15 | Example 16 | Example 17 | Example 18 |
|---|---|---|---|---|---|
| Polyvinyl alcohol | 14 | 12 | 10 | 10 | 8 |
| Propylene glycol | 5 | 5 | 5 | 5 | 5 |
| Ethanol | 5 | 5 | 5 | '5 | 5 |
| Liquid petrolatum | 10 | 15 | 25 | 35 | 50 |
| Preservative | Appropriate amount | Appropriate amount | Appropriate amount | Appropriate amount | Appropriate amount |
| Purified water | Balance | Balance | Balance | Balance | Balance |
| Drying time (minutes) | 17 | 13 | 10 | 7 | 7 |
| Usability | Δ | ○ | ⊙ | ⊙ | ○ |

TABLE 4

| Formulation | Comparative example 4 | Example 19 | Example 20 | Example 21 |
|---|---|---|---|---|
| Polyvinyl alcohol | 14 | 12 | 12 | 12 |
| Propylene glycol | 5 | 5 | 5 | 5 |
| Ethanol | 5 | 5 | 5 | 5 |
| Polymethylsiloxane | 10 | 15 | 15 | 15 |
| Polyoxyethylene lauryl ether | 0 | 1 | 3 | 10 |
| Preservative | Appropriate amount | Appropriate amount | Appropriate amount | Appropriate amount |
| Purified water | Balance | Balance | Balance | Balance |
| Drying time (minutes) | 17 | 10 | 6 | 6 |
| Usability | Δ | ○ | ⊙ | ⊙ |

TABLE 5

| Formulation | Example 22 | Example 23 | Example 24 |
|---|---|---|---|
| Polyvinyl alcohol | 10 | 10 | 10 |
| Propylene glycol | 5 | 5 | 5 |
| Ethanol | 5 | 5 | 5 |
| Polymethylsiloxane | 25 | 25 | 25 |
| Polyoxyethylene lauryl ether | 1 | 3 | 10 |
| Preservative | Appropriate amount | Appropriate amount | Appropriate amount |
| Purified water | Balance | Balance | Balance |
| Drying time (minutes) | 7 | 5 | 5 |
| Usability | ○ | ⊙ | ⊙ |

As clearly shown in Table 3, 4, and 5, the emulsion-type pack cosmetics of Examples which contain 15–50 wt % of the oil have a very short drying time and superior usability when peeled off compared with those of Comparative examples prepared with conventional technology. It has been shown that the drying time is further shortened when the surfactant is added, and that the usability further improves when the surfactant content is 3–10 wt %.

"Other Examples of the Invention Described in claim 1 in the Scope of the claim"

Example 25

A peel-off mask with the following composition was prepared.

| [Formulation] | |
|---|---|
| (1) Polyvinyl alcohol (degree of polymerization: 40 cps, degree of saponification: 88%) | 12 wt % |
| (2) Carboxymethyl cellulose | 2 |
| (3) 1,3-butylene glycol | 2 |
| (4) Dimethyl polysiloxane | 30 |
| (5) Citric acid | 0.1 |
| (6) Sodium citrate | 0.3 |
| (7) Ethanol | 10 |
| (8) Polyoxyethylene (16) 2-octyldodecyl ether | 1 |
| (9) Preservative | Appropriate amount |
| (10) Perfume | Appropriate amount |
| (11) Purified water | Balance |

[Preparation Method]

(1) through (6) were added to (11) and dissolved by heating and stirring at 80° C. (8) through (10), dissolved in (7), were added to and mixed with this, followed by cooling.

The obtained peel-off mask had a short drying time and good usability.

Example 26

A peel-off mask with the following composition was prepared.

| [Formulation] | |
|---|---|
| (1) Polyvinyl alcohol (degree of polymerization: 40 cps, degree of saponification: 88%) | 10 wt % |
| (2) Titanium oxide | 5 |
| (3) Glycerine | 2 |
| (4) Jojoba oil | 10 |
| (5) Squalane | 20 |
| (6) Ethanol | 10 |
| (7) Polyoxyethylene (20) sorbitan stearate | 1 |
| (8) Preservative | Appropriate amount |
| (9) Perfume | Appropriate amount |
| (10) Purified water | Balance |

[Preparation Method]

Preparation was carried out in the same manner as in Example 25.

The obtained peel-off mask had a short drying time and good usability.

Example 27

A peel-off mask with the following composition was prepared.

| [Formulation] | |
|---|---|
| (1) Polyvinyl alcohol (degree of polymerization: 40 cps, degree of saponification: 88%) | 10 wt % |
| (2) Xanthan gum | 0.5 |
| (3) Dimethyl polysiloxane | 35 |
| (4) Titanium oxide | 5 |
| (5) Talc | 10 |
| (6) Ethanol | 10 |
| (7) Preservative | Appropriate amount |
| (8) Perfume | Appropriate amount |
| (9) Purified water | Balance |

[Preparation Method]

Preparation was carried out in the same manner as in Example 25.

The obtained peel-off mask had a short drying time and good usability.

"Other Examples of the Invention Described in claim 2–claim 5 in the Scope of the claim"

Example 28

A peel-off mask with the following composition was prepared.

| [Formulation] | |
|---|---|
| (1) Polyvinyl alcohol | 12 wt % |
| (2) Propylene glycol | 3 |
| (3) Dimethylsiloxane | 20 |
| (4) Citric acid | 0.07 |
| (5) Sodium citrate | 0.03 |
| (6) Ethanol | 7 |
| (7) Polyoxyethylene dodecyl ether | 5 |
| (8) Preservative | Appropriate amount |
| (9) Perfume | Appropriate amount |
| (10) Purified water | Balance |

Example 29

A peel-off mask with the following composition was prepared.

| [Formulation] | |
|---|---|
| (1) Polyvinyl alcohol | 12 wt % |
| (2) 1,3 butylene glycol | 5 |
| (3) Squalane | 10 |
| (4) Liquid petrolatum | 10 |
| (5) Citric acid | 0.1 |
| (6) Polyoxyethylenesorbitansstearic ester | 6 |
| (7) Ascorbic acid | 3 |
| (8) Ethanol | 10 |
| (9) Preservative | Appropriate amount |
| (10) Perfume | Appropriate amount |
| (11) Purified water | Balance |

Example 30

A peel-off mask with the following composition was prepared.

| [Formulation] | | |
|---|---|---|
| (1) | Polyvinyl alcohol | 12 wt % |
| (2) | Xanthan gum | 0.1 |
| (3) | Glycerine | 3 |
| (4) | Dimethylpolysiloxane | 10 |
| (5) | Squalane | 5 |
| (6) | Jojoba oil | 7 |
| (7) | Polyoxyethylene lauryl ether | 5 |
| (8) | Tocopherol acetate | 0.1 |
| (9) | Ascorbic acid | 3 |
| (10) | Chelating agent | Appropriate amount |
| (11) | Preservative | Appropriate amount |
| (12) | Purified water | Balance |

INDUSTRIAL APPLICABILITY OF THE INVENTION

According to the present invention, a pack cosmetic with a short drying time after application of the pack and superior usability can be provided.

What is claimed is:

1. A fast drying peel-off pack cosmetic consisting of polyvinyl alcohol, water, and 20–80 wt % of one or more different oils selected from the group consisting of liquid petrolatum, squalane, and silicone oils, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

2. A fast drying peel-off pack cosmetic consisting of polyvinyl alcohol, water, and 15–50 wt % of one or more different oils selected from the group consisting of liquid petrolatum, squalane, and silicone oil, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

3. A fast drying peel-off pack cosmetic consisting of polyvinyl alcohol, water, and 25–40 wt % of one or more different oils selected from the group consisting of liquid petrolatum, squalane, and silicone oil, wherein a blend ratio of said polyvinyl alcohol is 9–15 wt % of the total amount of the pack cosmetic, said water being mixed with the other ingredients to form an emulsified composition, and said pack cosmetic having a short drying time which can then be smoothly peeled off after use.

4. A fast drying peel-off pack cosmetic consisting of polyvinyl alcohol, water, a surfactant, and 15–50 wt % of one or more different oils selected from the group consisting of liquid petrolatum, squalane, and silicone oil, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

5. A fast drying peel-off pack cosmetic consisting of polyvinyl alcohol, water, 1–20 wt % of a surfactant, and 15–50 wt % of one or more different oils selected from the group consisting of liquid petrolatum, squalane, and silicone oil, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

6. A fast drying peel-off pack cosmetic consisting of polyvinyl alcohol, water, 3–10 wt % of a surfactant, and 15–50 wt % of one or more different oils selected from the group consisting of liquid petrolatum, squalane, and silicone oil, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

7. A fast drying peel-off pack cosmetic consisting of polyvinyl alcohol, water, 10–30 wt % of a surfactant, and 20–80 wt % of one or more different oils selected from the group consisting of liquid petrolatum, squalane, and silicone oils, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

8. The fast drying peel-off pack cosmetic of claim 1, wherein the water constitutes 30–60 wt % of the total amount of the pack cosmetic.

9. The fast drying peel-off pack cosmetic of claim 2, wherein the water constitutes 30–60 wt % of the total amount of the pack cosmetic.

10. A fast drying peel-off pack cosmetic consisting of polyvinyl alcohol, water, and 20–80 wt % of one or more different oils selected from the group consisting of liquid petrolatum, squalane, and silicone oils, and one or more optional ingredients selected from the group consisting of lower alcohols, polyhydric alcohols, powders, water soluble polymers, preservatives, disinfectants, ultraviolet light absorbents, chellating agents, antioxidants, perfumes, and combinations thereof, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

11. A fast drying peel-off pack cosmetic consisting of polyvinyl alcohol, water, 15–50 wt % of one or more different oils selected from the group consisting of liquid petrolatum, squalane, and silicone oils, and one or more optional ingredients selected from the group consisting of lower alcohols, polyhydric alcohols, powders, water soluble polymers, preservatives, disinfectants, ultraviolet light absorbents, chellating agents, antioxidants, perfumes, and combinations thereof, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

12. A fast drying peel-off pack cosmetic consisting of polyvinyl alcohol, water, 25–40 wt % of one or more different oils selected from the group consisting of liquid petrolatum, squalane, and silicone oils, and one or more optional ingredients selected from the group consisting of lower alcohols, polyhydric alcohols, powders, water soluble polymers, preservatives, disinfectants, ultraviolet light absorbents, chellating agents, antioxidants, perfumes, and combinations thereof, wherein a blend ratio of said polyvinyl alcohol is 5–20 wt % of the total amount of the pack cosmetic, said water being mixed with the other ingredients to form an emulsified composition, and said pack cosmetic having a short drying time which can then be smoothly peeled off after use.

* * * * *